(12) United States Patent
Vinikova et al.

(10) Patent No.: US 6,251,946 B1
(45) Date of Patent: Jun. 26, 2001

(54) BRANCHED CHAIN FATTY ACIDS, THEIR DERIVATIVES AND USE IN THE TREATMENT OF CENTRAL NERVOUS SYSTEM DISORDERS

(75) Inventors: Marina Vinikova, Ramla; Alexander Kozak, Rehovot; Israel Shapiro, Ramla, all of (IL)

(73) Assignee: D-Pharm Ltd., Rehovot (IL)

( * ) Notice: Subject to any disclaimer, the term of this patent is extended or adjusted under 35 U.S.C. 154(b) by 0 days.

(21) Appl. No.: 09/462,533

(22) PCT Filed: Jul. 7, 1998

(86) PCT No.: PCT/IL98/00316
§ 371 Date: Apr. 11, 2000
§ 102(e) Date: Apr. 11, 2000

(87) PCT Pub. No.: WO99/02485
PCT Pub. Date: Jan. 21, 1999

(30) Foreign Application Priority Data

Jul. 9, 1997 (IL) .................................................. 121268

(51) Int. Cl.$^7$ ............................................. A01N 37/18
(52) U.S. Cl. .............................. 514/613; 554/35; 554/79; 562/512; 564/192
(58) Field of Search .............................. 514/613; 554/35, 554/79; 562/512; 564/192

(56) References Cited

U.S. PATENT DOCUMENTS 4,846,991  7/1989  Suzue et al. .................. 252/89.1
5,278,300  1/1994  Hasegawa et al. ............. 536/53

OTHER PUBLICATIONS

Chemical Abstracts: vol. 126, No. 8, Feb. 24, 1997, p. 1018, col. 2, abstract No. 108640t, Jacob et al., "Branched Carboxylic Acid Esters as Antibacterial, Antifungal, and Antiviral Agents."

Chemical Abstracts: vol. 122, No. 13, Mar. 27, 1995, p. 948, col. 2, abstract No. 160096b, Ohuchida et al., "Preparation of Valprate Analogs as Neuroprotectants."

Primary Examiner—Deborah D. Carr
(74) Attorney, Agent, or Firm—Davidson, Davidson & Kappel, LLC

(57) ABSTRACT

A compound having formula (I): wherein $R_1$ is a saturated or unsaturated chain of 1–5 carbons in length; and $R_2$ is a saturated or unsaturated chain of 3–10 carbons in length; and A is selected from the group consisting of COOL and CONR'—R", wherein L is a lipid moiety selected from the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lyso plasmalogens, lysophospholipids, lysophosphatidic acid amides, glycerophosphoric acids, sphingolipids, lysophosphatidylethanolamines, and N-mono and N,N-di-($C_{1-4}$)alkyl derivatives of the amines thereof; and R' and R" are each independently selected from the group consisting of hydrogen and a lower alkyl group comprising 1–5 carbon atoms; and pharmaceutically acceptable salts thereof. In addition, there is provided methods for using these compositions.

(I)

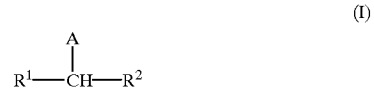

28 Claims, 2 Drawing Sheets

BRANCHED CHAIN FATTY ACIDS, THEIR DERIVATIVES AND USE IN THE TREATMENT OF CENTRAL NERVOUS SYSTEM DISORDERS

This application is a 371 of PCT/IL98/00316 filed Jul. 7, 1998.

FIELD OF THE INVENTION

The present invention relates to a family of valproic acid analogs, to prodrugs of these compounds, to pharmaceutical compositions thereof and to their use for treating epilepsy, migraine, bipolar disorders or pain.

BACKGROUND OF THE INVENTION

Many of the most prevalent diseases in humans including ischemia, stroke, epilepsy, asthma and allergy are all believed to be related to the phenomenon of cell hyperexcitation, a term used herein to denote supranormal intracellular enzyme activity.

Epilepsy in particular is characterized by transitory high levels of abnormal neurological activity or seizures, referred to as the ictal state. The interictal state is manifested by a period of relative quiescence. Types of seizures include partial, or focal seizures, which are restricted to a particular locus within the brain; and generalized seizures, which can result in abnormal activity throughout the brain. Generalized seizures include tonic-clonic, or grand mal, seizures, in which the entire body undergoes convulsions. Left untreated, epilepsy can degenerate into status epilepticus a potentially fatal neurological emergency [*Antiepileptic Drugs;* eds. R. H. Levy, R. H. Mattson and B. S. Meldrum; 4$^{th}$ Edition, Raven Press, NY, N.Y.].

Because of the potential dangers of epilepsy, many different types of therapeutic modalities have been proposed. However, the effective treatment of epilepsy has been hampered by the side effects of many medications. For example, some anti-epileptic medications, such as phenobarbital, are sedating [*Antiepileptic Drugs;* eds. R. H. Levy, R. H. Mattson and B. S. Meldrum; 4$^{th}$ Edition; Raven Press, NY, N.Y.; p. 130–131]. Others, such as valproic acid, are hepatotoxic, have teratogenic effects and may interact with other therapeutic drugs. Certain anti-epileptic medications have dangerous systemic effects, such as potentially fatal aplastic anemia, hepatotoxicity and connective tissue abnormalities [*Antiepileptic Drugs;* eds. R. H. Levy, R. H. Mattson and B. S. Meldrum; 4$^{th}$ Edition; Raven Press, NY, N.Y.; p. 130–131]. Such dangerous side effects are a direct consequence of drugs which have broad systemic delivery and absorption.

These dangerous side effects restrict the therapeutic use of otherwise effective drugs. For example, valproic acid is highly effective against several types of generalized seizures, including absence, generalized tonic-clonic and myoclonic seizures [*Antiepileptic Drugs;* eds. R. H. Levy, R. H. Mattson and B. S. Meldrum; 4$^{th}$ Edition, Raven Press, NY, N.Y.]. Valproic acid was clinically shown to be effective against epilepsy in many patients who have proven to be refractory to other treatments. Valproic acid has also been found to be an effective prophylactic against migraines and bipolar disorders, as well as in the treatment of central pain [Shelton C E, Connelly J F, "Valproic acid: a migraine prophylaxis alternative", *Ann Pharmacother,* 30:865–866, 1996; Cutrer F M, and Moskowitz M A, "The actions of valproate and neurosteroids in a model of trigeminal pain", *Headache,* 36:579–585, 1996; and Keck P E Jr, McElroy S L and Strakowski S M, "New developments in the pharmacologic treatment of schizoaffective disorder" *J Clin Psychiatry,* 57 Suppl 9:41–48., 1996). Unfortunately, as noted above, valproic acid and many of its analogs have a number of side effects, including: tremors, sedation, irritability, neutropenia, bone marrow suppression, hepatotoxicity, teratogenic effects, and metabolic disturbances including hyperammonemia-a condition which itself can cause seizures [*Antiepileptic Drugs;* eds. R. H. Levy, R. H. Mattson and B. S. Meldrum; 4$^{th}$ Edition, Raven Press, NY, N.Y.]. Clearly, developing a form of valproic acid which is substantially free of these effects would be highly useful.

Side effects of anti-epileptic medications can be divided into two general groups. The first group includes unwanted neurological effects, such as sedation. The second, and occasionally fatal, group includes systemic effects such as hepatic dysfunction and aplastic anemia. Both groups of side effects result from a combination of delivery of the active molecule to tissues other than diseased neurons and the ability of the active molecule to alter the normal function of these tissues. Thus, both groups of side effects are amenable to amelioration by restriction of the delivery of the active drug molecule only to diseased cells to be treated and by modification of the pharmacophore to eliminate effects on normal tissues.

One strategy which limits the delivery of the active drug molecule to the desired site of action is disclosed in International Patent Application WO 94/22483, filed Mar. 30, 1994, herein incorporated by reference. According to this disclosure, the drug is selectively activated in those diseased cells which exhibit specific enzyme hyperactivity. The pharmacologically active molecule is administered in the form of an inactive prodrug which is designed to be cleaved preferentially by the excess enzyme activity, so that the pharmacologically active molecule accumulates at the diseased site rather than in healthy cells. Such targeting was shown to effectively treat the pathological state of the diseased cells, with far fewer effects on the normal cells.

Although many different types of prodrugs are possible, WO 94/22483 disclosed cell permeable prodrugs, composed of a pharmacologically active compound covalently bound to a lipophilic moiety which facilitates intracellular transport of the prodrug. Hereinafter the term "prodrug" denotes a molecule which has either little or no pharmacological activity of the active compound. The active compound will exert its therapeutic effects after it is released from the prodrugs of the invention by the action of intracellular enzymes. The covalent bond of these prodrugs are scission sensitive to enzymes that are hyperactive in the cells that are affected, thereby providing selective activation of the pharmacological compound in the diseased cells.

One group of intracellular enzymes of particular relevance in the pathogenesis of epilepsy and ischemic injury are the phospholipases, especially phospholipase A$_2$ (PLA$_2$). In excitatory disorders such as epilepsy, phopholipase activity increases many fold.

Phospholipase A$_2$ demonstrates a sustained increase in activity during the ictal and postictal period, although other phospholipases may also be involved in the pathogenesis of epilepsy. WO 94/22483 discloses a prodrug form of valproic acid, called TVA, which is scission-sensitive to PLA$_2$. Chemically, TVA comprises valproic acid covalently linked as an ester to a phosphatidylcholine moiety ROCH$_2$—CH(OH)—CH$_2$O—(PO$_2$)—O(CH$_2$)$_2$N(CH$_3$)$_3$, wherein R is hexadecanoyl. Clearly such prodrugs can be activated within the body and exert a pharmacological effect. In a mouse experimental model, TVA was shown to have significant anticonvulsant activity and to be more than 10 times as potent as sodium valproate.

A second strategy for both enhancing efficacy and eliminating side effects of drugs is the modification or alteration of a "lead compound" to produce a novel molecule which has the desired therapeutic effect without the unwanted side effects. Such an approach is widely used in drug design. Unfortunately, rational drug design is limited by the lack of knowledge with regard to biological drug interactions, and in particular the lack of three-dimensional structures for specific cell components, such as receptors, with which the drugs interact. Thus, although valproic acid has been widely studied, altered forms of this drug have not yet been found which eliminate the side effects.

There is therefore a need for, and it would be highly advantageous to have, analogs of valproic acid which substantially lack systemic side effects.

SUMMARY OF THE INVENTION

It is an object of the present invention to provide saturated or unsaturated branched fatty acid compounds to treat central nervous system disorders, including but not limited to epilepsy, migraines, chronic pain and bipolar disorders.

According to the teachings of the present invention, there is provided a compound having a formula (I):

(I)

wherein:

$R_1$ is a saturated or unsaturated chain of 1–5 carbons in length; and $R_2$ is a saturated or unsaturated chain of 3–10 carbons in length; and A is selected from the group consisting of COOL and CONR'—R", wherein L is a lipid moiety selected from the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lyso plasmalogens, lysophospholipids, lysophophatidic acid amides, glycerophosphoric acids, sphingolipids, lysophosphatidylethanolamine, and N-mono and N,N-di-$(C_{1-4})$alkyl derivatives of the amines thereof; and R' and R" are each independently selected from the group consisting of hydrogen and a lower alkyl group comprising 1–5 carbon atoms;

and pharmaceutically acceptable salts thereof. Preferably, $R_1$ is $(CH_2)_nCH_3$, n being 0–4; $R_2$ is $(CH_2)_xCH_3$, x being 2–9. Even more preferably, n is 2 and x is 6 or 9. Most preferably, n is 2 and x is 6. Preferably, A is COOL.

According to another embodiment of the present invention, there is provided a composition for treating a central nervous system disorder, comprising a pharmaceutically effective amount of a compound in combination with a pharmaceutically acceptable carrier, said compound being a member of a group having the formula (I):

(I)

wherein:

$R_1$ is a saturated or unsaturated chain of 1–5 carbons in length; and $R_2$ is a saturated or unsaturated chain of 3–10 carbons in length; and A is selected from the group consisting of COOL and CONR'—R", wherein L is a lipid moiety selected from the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lyso plasmalogens, lysophospholipids, lysophophatidic acid amides, glycerophosphoric acids, sphingolipids, lysophosphatidylethanolamine, and N-mono and N,N-di-$(C_{1-4})$alkyl derivatives of the amines thereof; and R' and R" are each independently selected from the group consisting of hydrogen and a lower alkyl group comprising 1–5 carbon atoms; and pharmaceutically acceptable salts thereof.

According to yet another embodiment of the present invention, there is provided a method for the treatment of a central nervous system disorder in a subject, comprising the step of administering a pharmaceutically effective amount of a compound having the formula (I):

(I)

wherein:

$R_1$ is a saturated or unsaturated chain of 1–5 carbons in length; and $R_2$ is a saturated or unsaturated chain of 3–10 carbons in length; and A is selected from the group consisting of COOL and CONR'—R", wherein L is a lipid moiety selected from the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lyso plasmalogens, lysophospholipids, lysophophatidic acid amides, glycerophosphoric acids, sphingolipids, lysophosphatidylethanolamine, and N-mono and N,N-di-$(C_{1-4})$alkyl derivatives of the amines thereof; and R' and R" are each independently selected from the group consisting of hydrogen and a lower alkyl group comprising 1–5 carbon atoms; and pharmaceutically acceptable salts thereof.

According to still another embodiment of the present invention, there is provided a compound having a formula (II):

(II)

wherein:

$R_1$ is a saturated or unsaturated chain of 1–5 carbons in length; and $R_2$ is a saturated or unsaturated chain of 3–10 carbons in length, with the proviso that $R_1$ is not C≡CH, CH=CH$_2$ or CH$_2$—CH$_3$; with the proviso that when is $R_1$ is 3 carbons in length, $R_2$ is a chain of 4–10 carbons in length; and with the proviso that when $R_1$ is $C_3H_7$, $R_2$ is not $C_3H_7$, $C_6H_9$ or $C_5H_{11}$; when $R_1$ is $C_4H_9$, $R_2$ is not $C_4H_9$; and B is selected from the group consisting of COOH and COO$^-$Y+, wherein Y denotes any pharmaceutically acceptable counter-ion;

and pharmaceutically acceptable salts thereof.

According to a currently preferred embodiment of the invention, $R_1$ is (CH$_2$)$_n$CH$_3$, n being 0–4; $R_2$ is (CH$_2$)$_x$CH$_3$, x being 2–9, with the proviso that when n is 2, x is 3–9. More preferably, n is 2 and x is 6 to 9.

Within the scope of the present invention, the branched chain fatty acid compounds may be used as free acids, their physiologically acceptable salts or mixtures thereof, esters and amides. Furthermore, for those compounds having a chiral center of asymmetry, the compounds of the present invention include optically active isomers, racemates or preferred mixtures thereof.

DESCRIPTION OF THE INVENTION

The present invention relates to novel fatty acid molecules, compositions and methods for the treatment of epilepsy and other neurological disorders. These novel molecules and compositions have reduced side effects as further described below. The fatty acids of the present invention may be saturated or unsaturated. The saturated branched fatty acids according to the present invention are also known as 2-alkyl fatty acids or dialkyl acetic acids or 2-alkylalkanoic acids or 2-alkylalkanoates. In addition, as noted previously the branched chain fatty acid compounds may be used as free acids, their physiologically acceptable salts or mixtures thereof, esters and amides. Furthermore, for those compounds having a chiral center of asymmetry, the compounds of the present invention include D and L isomers, racemates or preferred mixtures thereof.

Furthermore, since these molecules are related to valproic acid, and the efficacy of valproic acid as a treatment for epilepsy was predictive for its ability to ameliorate other disease states such as migraines, chronic pain and bipolar disorders, it is anticipated that these novel molecules and compositions will have a similar breadth of therapeutic activity.

There are three related families of molecules within the present invention. The first family includes compounds of the formula (I):

(I)

wherein:
$R_1$ is a saturated or unsaturated chain of 1–5 carbons in length; and
$R_2$ is a saturated or unsaturated chain of 3–10 carbons in length; and
A is selected from the group consisting of COOL and CONR'—R", wherein L is a lipid moiety selected from the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lyso plasmalogens, lysophospholipids, lysophophatidic acid amides, glycerophosphoric acids, sphingolipids, lysophosphatidylethanolamine, and N-mono and N,N-di-($C_{1-4}$)alkyl derivatives of the amines thereof; and R' and R" are each independently selected from the group consisting of hydrogen and a lower alkyl group comprising 1–5 carbon atoms;

and pharmaceutically acceptable salts thereof.

Without wishing to be limited to a single mechanism, those compounds in which A is COOL are preferred for those advantages described above and given in greater detail below. Those compounds in which A is CONR'—R" are preferred because these compounds may be both lipophilic yet slightly basic, thereby potentially enhancing transport across the cellular membrane, again without wishing to be limited to a single mechanism.

It should be noted that if $R_1$ is 3 carbons in length and $R_2$ is a chain of 3 carbons in length, and the group A is substituted by "COOH", the resultant molecule is valproic acid. Therefore, this family of molecules includes valproic acid analogs which include a lipid or amide moiety in place of the hydrogen atom of the carboxyl group of valproic acid. This family of molecules has been designed to bind to or interact with the same neurological components which are required for therapy with valproic acid, yet to avoid systemic interactions which cause the debilitating side effects of valproic acid. By changing the number of carbon atoms in each chain and by adding the lipid or amide moiety, greater specificity is potentially achieved substantially without reducing therapeutic efficacy.

The addition of the lipid moiety transforms these molecules into prodrugs, which as noted above are cleavable by an enzyme displaying excessive levels of activity in diseased cells. Generally speaking, the pharmacophore (in this case one of the members of the first family of molecules) is activated after being cleaved from the lipid moiety. This process is hereinafter described as "RAP" for regulated activation of prodrug. The activation is regulated in the sense that a specific enzyme is required for the parent molecule to be released. Thus, the subject is not systemically exposed to high levels of the generally active form of the drug.

The type of lipid moiety selected clearly depends upon the specificity of the enzyme, most probably a phospholipase, which will cleave the molecule for the RAP process to occur. Distinction among the various phospholipases is based in part on their substrate specificity as well as their tissue localization, regulation and physicochemical attributes. The different specificities of these classes of phospholipases can serve as the basis of designing prodrugs which undergo specific activation, as suitable for the pathology to be treated.

The cleavage sites of the various phospholipases are herein depicted schematically in the following scheme 1.
Scheme 1

In the prodrugs of the present invention it is possible to covalently join the pharmacologically active compound to any of the positions that will be cleaved by the different phospholipases, as depicted. Thus, a drug which is a carboxylic acid can be joined at positions sn-3, sn-2 or in place of the polar head group of the phospholipid, to be released by the respective phospholipases.

The choice of the preferred fatty acid residue, in position sn-1, that is appropriate for any given prodrug is dependent on the intended therapeutic use of the conjugate. Thus fatty acid residues where $R_1$ is a carbon chain of length below $C_{10}$ exhibit very low substrate specificity, but fatty acid residues where $R_1$ is a carbon chain of length above $C_{12}$–$C_{14}$ are very good substrates for the phospholipases and will therefore be readily activated. Regulated activation will best be achieved by the intermediate length fatty acid residues, and these will be preferred for the treatment of persistent or chronic disease states or disorders.

In contradistinction, in certain disease states that require the rapid release of the active agent the most preferred will be the longer chain fatty acid residues. This is most suitable for conditions involving acute onset pathology such as in the treatment of epilepsy with the prodrugs of the invention.

A most preferred embodiment of the invention utilizes drugs joined to the phospholipid via sn-2 linkages that are digested by phospholipases A2, as discussed above. In disorders such as epilepsy, PLA2 activation coincides with epileptic seizures.

Phospholipases A2 are a family of esterases that hydrolyze the sn-2 ester bonds in phosphoglyceride molecules releasing a free fatty acid and a lysophospholipid. Classification of the members of this family of enzymes is based on certain structural features and/or their localization in different cells and tissues. In principle, these enzymes are more active on aggregated phospholipid substrates compared with monomeric soluble substrates.

The second family of molecules does not have the additional lipid moiety in place of the hydrogen atom of the carboxyl group. Instead, this family has the following formula (II):

(II)

wherein:
$R_1$ is a saturated or unsaturated chain of 1–5 carbons in length; and
$R_2$ is a saturated or unsaturated chain of 3–10 carbons in length, with the proviso that $R_1$ is not
C≡CH, CH=$CH_2$ or $CH_2$—$CH_3$; with the proviso that when is RI is 3 carbons in length, $R_2$ is a chain of 4–10 carbons in length; and with the proviso that when $R_1$ is $C_3H_7$, $R_2$ is not $C_3H_7$, $C_6H_9$ or $C_5H_{11}$; when $R_1$ is $C_4H_9$, $R_2$ is not $C_4H_9$;
and B is selected from the group consisting of COOH and $COO^-Y^+$, wherein Y denotes any pharmaceutically acceptable counter-ion;
and pharmaceutically acceptable salts thereof.

It should be noted that if $R_1$ is 3 carbons in length and $R_2$ is a chain of 3 carbons in length, the resultant molecule is valproic acid. This family of molecules has been designed to bind or interact with the same neurological components which are required for therapy with valproic acid, yet to avoid systemic interactions which cause the debilitating side effects of valproic acid. By changing the number of carbon atoms in each chain, greater specificity is achieved substantially without reducing therapeutic efficacy, as further described below. Thus, unexpectedly these members of the family of compounds of formula (II) cause less severe side effects than valproic acid in an animal model.

Of the preferred members of both the compounds of formula (I) and formula (II), the more preferred compounds are those in which the substituent $R_1$ is not identical to the substituent $R_2$. The most preferred compounds are those compounds wherein $R_1$ is $CH_{2(2)}CH_3$ and $R_2$ is $CH_{2(6)}CH_3$. Of course, all of these groupings of preferred members also include those compounds which are free acids, their physiologically acceptable salts or mixtures thereof, esters and amides. Furthermore, for those compounds having a chiral center of asymmetry, these preferred members also include all enantiomers including but not limited to optically active D and L isomers, racemates or preferred mixtures thereof.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention relates to a group of compounds analogous to valproic acid, namely a family of branched fatty acids and their analogs, to pharmaceutical compositions of these compounds, and to their use in the treatment of neurological disorders. Some of these compounds are novel and are claimed as such.

The compositions according to the invention display strong antiepileptic activity in an experimental mouse model of epilepsy, yet lack many of the systemic side effects of valproic acid.

The principles and operation of the anti-epileptic compounds according to the present invention may be better understood with reference to the Examples, Figures and the accompanying description.

EXAMPLE 1

Synthesis of M-VPA Molecules

As noted above, it would be highly advantageous to have anti-epileptic drugs with more selective activity against diseased cells. Examples of such drugs are provided by the family of molecules denoted herein as the M-VPA molecules. These molecules are branched fatty acids or amides which are preferably asymmetric and most preferably saturated. The M-VPA family of molecules can be defined according to the following formula (III):

(III)

in which $R_1$ and $R_2$ are each defined according to the number of carbons in an alkyl chain. For example, VPA itself would be described as M(3,3), indicating that $R_1$ and $R_2$ both have the formula $CH_2$—$CH_2$—$CH_3$. The specific molecules tested include M(3,7); M(3,10); M(7,7); M(7,10); M(7,14); M(10,10); M(10,14); and M(14,14).

For the sake of clarity, the following discussion will be limited to the saturated members of the M-VPA family, it being understood that unsaturated M-VPA molecules could also be used.

Synthesis of Propylheptylacetic Acid [M(3,7)].

The synthesis of propyl heptylacetic acid is a four-stage procedure. Alkylation of diethyl ester of malonic acid is the first stage. The second stage is alkylation of diethyl propylmalonate. Hydrolysis of diethyl ester of dialkylmalonic acid is third stage. The final product (propylheptylacetic acid) is prepared by decarboxylation of the corresponding dialkylmalonic acid.

Stage 1. Synthesis of Diethyl Propylmalonate.

$CH_2(CO_2C_2H_5)_2 + NaH \rightarrow NaCH(CO_2C_2H_5)_2 + H_2$   1.

$NaCH(CO_2C_2H_5)_2 + n\text{-}C_3H_7Br \rightarrow n\text{-}C_3H_7\text{---}CH(CO_2C_2H_5)_2 + NaBr$   2.

Sodium hydride (8.25 gr., 0.344 Mol) under argon is introduced into a two-neck flask (1 L), equipped with a magnetic stirrer and a reverse condenser (water cooling). Also under argon tetrahydrofuran (THF, 100 ml) is introduced into the flask. THF is freshly distilled under $LiAlH_4$. The drop funnel is joined to the flask and the solution of diethyl malonate (47.4 ml, 0.312 Mol) in THF (150 ml) is added drop-by-drop to the mixture of NaH with THF. The mixture is stirred by magnetic stirrer during the process of addition, and for some time thereafter until hydrogen bubbles evolve from the mixture. Then a solution of propyl bromide (28.4 ml, 0.313 Mol) in THF (50 ml) is added drop-by-drop. In order to complete the reaction the mixture is heated to 80–90° C. After 5 hours the mixture is cooled down to room temperature and the unreacted sodium hydride is decomposed by ethanol (50 ml). The precipitate is filtered and the obtained solution is evaporated under vacuum (about 25 mm Hg). The residue is dissolved in petroleum ether (200 ml) and this solution is washed three times by water (each portion is 100 ml) in a separated funnel. The organic phase is dried by $MgSO_4$ for 8 hours and petroleum ether is distilled under vacuum. Yield of diethyl propylmalonate is 80%, namely 50.5 gr (0.250 Mol).

TLC analysis: Silica gel 60 F254 on aluminum sheet. Eluent is a mixture of petroleum ether with diethyl ether (9:1 v/v). Chromatogram is sprayed with indicator spray and then is charred at 100–150° C. Composition of indicator spray: 4-methoxybenzaldehyde (10 ml), ethanol (200 ml), 98% $H_2SO_4$ (10 ml) and glacial acetic acid (2 ml). One spot is visible in UV spectra. $R_f=0.54$.

Stage II. Synthesis of Diethyl Propylheptyl Malonate.

$n\text{-}C_3H_7\text{---}CH(CO_2C_2H_5)_2 + NaH \rightarrow n\text{-}C_3H_7\text{---}CNa(CO_2C_2H_5)_2 + H_2$   1.

$n\text{-}C_3H_7\text{---}CNa(CO_2C_2H_5)_2 + n\text{-}C_7H_{15}Br \rightarrow (n\text{-}C_3H_7)C(n\text{-}C_7H_{15})(CO_2C_2H_5)_2 + NaBr$   2.

The procedure of introduction of heptyl radical into a molecule of diethyl propylmalonate is analogous to the procedure of propyl radical introduction into a molecule of diethyl malonate (1 stage). For alkylation of 50.5 gr. (0.250 Mol) of diethyl propylmalonate we used 6.6 gr (0.275 Mot) of sodium hydride and 45 gr. (0.250 Mol) of n-heptyl bromide. Yield of diethyl propylheptylmalonate is 80%, namely 60 gr. (0.200 Mol).

TLC analysis: Conditions of analysis of diethyl propylheptylmalonate are the same as the analysis of diethyl propylmalonate. One spot is visible in UV spectra. Rf=0.7.

Stage III. Hydrolysis of Diethyl Propylheptylmalonate.

$n\text{-}C_3H_7\text{---}C(n\text{-}C_7H_{15})(CO_2C_2H_5)_2 + 2H_2O \rightarrow n\text{-}C_3H_7\text{---}C(n\text{-}C_7H_{15})(CO_2H)_2 + 2C_2H_5OH$ Diethyl propylheptylmalonate (60 gr., 0.200 Mol), potassium hydroxide (67.2 gr., 1.2 Mol), water (68.5 gr., 3.8 Mol) and ethanol (142.5 gr., 2.3 Mol) are introduced into a round-bottom one-neck flask (0.5 L), equipped with a magnetic stirrer and a reverse condenser. The reaction mixture is heated in oil bath for 4 hours at 90° C. After cooling, the mixture is transferred to a separated funnel and the unreacted diethyl propylheptylmalonate is extracted by petroleum ether (two portions, each portion is 150 ml). The water solution is cooled by ice and is acidified by concentrated hydrochloric acid up to pH 1–2. The obtained propylheptylmalonic acid is extracted from water by chloroform (three times, each portion is 100 ml) and is dried by $MgSO_4$. Chloroform is evaporated under vacuum. Yield of propylheptylmalonic acid is 90% (43.9 gr., 0.18 Mol).

TLC analysis: Silica gel 60 F254 on aluminum sheet. Eluent is mixture of chloroform with methanol (95:5 v/v). Chromatogram is sprayed with indicator spray and is charred at 100–150° C. For composition of spray see stage I. One spot is visible in WV spectra. $R_f=0.17$.

Stage IV. Decarboxylation of Propylheptylmalonic Acid.

$n\text{-}C_3H_7\text{---}C(n\text{-}C_7H_{15})(CO_2H)_2 \rightarrow n\text{-}C_3H_7\text{---}CH(n\text{-}C_7H_{15})COOH + CO_2$ Propylheptylmalonic acid (43.9 gr., 0.18 Mol) is introduced into a round-bottom single-neck flask (0.250 L) and is heated by oil bath at 160–170° C. until bubbles of $CO_2$ are no longer visible. For completion of the reaction, the flask is joined to a vacuum line (about 40 mm Hg) and is heated at 120–130° C. for 0.5 hour. The obtained propylheptylacetic acid is purified by vacuum distillation. b.p. 125° C. (1 mm Hg). The yield was 70%, namely 25.2 grams (0.125 Mol).

Analysis by TLC: Silica gel 60 F254 on aluminum sheet. Eluent is mixture of chloroform with methanol (95:5 v/v). Chromatogram is sprayed by indicator spray and is charred at 100–150° C. Composition of spray see stage I. One spot. Rf 0.58

Elementary analysis. $C_{12}H_{24}O_2$. Calculated: C 72.00%, H 12.00%. Found: C 71.82%, H 12.28%.

$1_H$ NMR (CDCL3), δ (ppm): 0.85–0.95 (m, 6H), 1.28 (broad s, 12H), 1.33–1.50 (m, 2H), 1.59–1.65 (m, 2H), 2.36 (m, 1H).

The procedure of preparation of other dialkylacetic acids is analogous to synthesis of propylheptylacetic acid.

EXAMPLE 2

Standardized Tests for Anti-epileptic Drugs

A number of standardized tests are employed in order to examine potential new anti-epileptic drugs. These tests were developed in accordance with the Epilepsy Branch of the National Institute of Neurological Disorders and Stroke (National Institutes of Health, USA), in order to provide a "gold standard" for measuring the efficacy of new anti-epileptic molecules. The following description was taken from Chapter 7 of *Antiepileptic Drugs*, "Experimental Selection, Quantification, and Evaluation of Antiepileptic Drugs", incorporated by reference herein [eds. R. H. Levy, R. H. Mattson and B. S. Meldrum; 4$^{th}$ Edition, Raven Press, NY, N.Y.; pages 99–110].

One animal model of epilepsy is PTZ-induced seizures in mice, which is used to test the drugs and prodrugs of the present invention. In this model, mice are injected subcutaneously with pentylenetetrazol (PTZ), which causes severe seizures and even death. The potential new anti-epileptic drug is injected before PTZ is given, and the mice are observed for the ability of the new drug to prevent seizure occurrence, the tendency towards sedation or excitability, and for the behavior of the mice in the rotorod test. The experimental details are as follows.

The test drug is injected first through the intraperitoneal route of administration, at levels specifically given below, in 0.9% saline solution or in triolein oil. The volume given is 0.01 ml/g body weight. PTZ is prepared by dissolution in 0.9% saline for a 0.85% PTZ solution. The dosage level of PTZ is 85 mg/kg body weight of the mouse to be injected. After the test drug has been injected, the mouse is subjected to the rotorod test. PTZ is then injected and the mouse is observed for seizure activity for one hour. The survival rate following PTZ treatment is also determined.

Efficacy of each tested drug was assessed by comparison to the effect of valproic acid.

EXAMPLE 3

Anti-Convulsive Effect of M-VPA

Valproic acid (VPA) is a highly effective anti-epileptic drug with a broad spectrum of activity, as described above. However, it also has a number of side effects, such as teratogenicity, weight gain and hepatic dysfunction and toxicity, which range in seriousness from minor to extremely dangerous. Clearly, it would be advantageous to be able to target the anti-epileptic effects of VPA to those diseased neurons which initially generate the seizure activity, thereby reducing or eliminating the unwanted systemic effects.

As noted above, one form of targeting involves the manipulation of the pharmacophore to eliminate unwanted systemic effects, and promote the desired treatment effects. The synthesis of a number of different members of the M-VPA family, which are VPA analogs, is given above.

Members of the M-VPA family were synthesized and tested for their effectiveness in the prevention of seizures in mice. The goal was to define those molecules which were therapeutically effective yet which were relatively free of side effects.

The desired outcome was the ability of the drug molecule to reduce or abolish PTZ-induced seizures substantially without sedating effects. The experimental method was as follows.

Male Sabra mice weighing 30–40 gm were used for these experiments. Animals were maintained on an adequate diet and allowed free access to food and water except briefly during the experimental period. Animals were separately housed for one hour in transparent plastic cages before treatment and during the experimental period. For the actual experiments, the mice were given an i.p. (intra-peritoneal) injection of either a M-VPA molecule or VPA itself as a control. All drugs were given in solution with a concentration of 0.35 M at the dosage of 0.01 ml/ gm body weight in triolein (3.5 mmol/kg), 60 minutes before the PTZ threshold seizure test (described above). Both the sedative and anti-convulsant effects of the molecules were examined. Each experimental condition was studied in three mice.

The anti-convulsant effects were determined by both the number of convulsions per mouse on average, and the mortality rate from the convulsions. In general, PTZ induced at least two generalized convulsions in the control (untreated) mice, with a 50% mortality rate. Death usually occurred after the second convulsion. Control mice, injected with the vehicle, did not manifest excited behavior. The results are given in Table 1.

TABLE 1

Efficacy of M-VPA Molecules
These compounds were in the free acid form, dissolved in triolein

| Compound | Dose (mg/kg) | Protection (number protected/total number) |
| --- | --- | --- |
| M(3,7) | 694 | 7/7 |
| M(3,10) | 840 | 3/10 |
| M(7,7) | 889 | 0/3 |
| M(7,10) | 1034 | 0/3 |
| M(7,14) | 1229 | 0/3 |
| M(10,10) | 1180 | 0/3 |
| M(10,14) | 1375 | 1/6 |
| M(3,14) | 1034 | 0/8 |

The key for Table 1 is as follows. Each drug was given at a concentration which was the molar equivalent to 500 mg/kg VPA, and therefore varied according to the molecular weight of the particular drug. Each drug was then rated for resultant anti-convulsive behavior in terms of the number of animals protected (the first term of the ratio) versus the total number of animals tested (the second term of the ratio).

Figure 1:
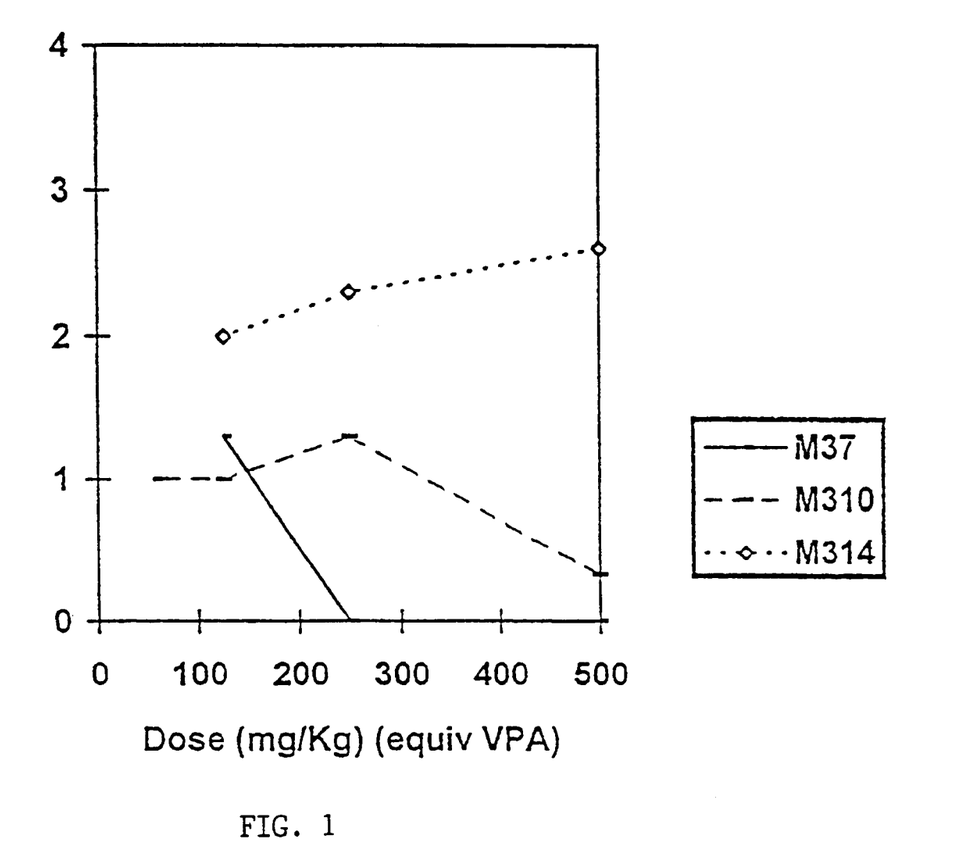
FIG. 1 is a graph illustrating dose-response to compounds of the present invention.

FIG. 1 shows a dose-response curve with M(3,7) and M(3,10). The x-axis is the dose of each drug, mg/kg body weight as the equivalent of VPA. The y-axis is the number of seizures per animal. Each point represents an average of three mice, except for the second concentration of M(3,7), which represents five mice. As noted above, animals given PTZ alone generally had at least two generalized convulsions. High doses of M(3,10) substantially reduced the level of seizure activity. M(3,7) was the most effective at preventing seizure activity.

From these results, the following observations can be made. First, the best anti-convulsive activity was shown by VPA, M(3,7) and M(3,10). All of these share the structure of $R_1$ being a saturated tricarbon chain, while the length of $R_2$ varies. Interestingly, the anti-convulsive properties of the M-VPA molecule appear to be directly related to the length of $R_2$, with effective anti-convulsive activity seen up through and including 10 methyl groups. Increasing the length of $R_1$ from 3 to 7 carbons abolishes all anti-convulsant activity.

If $R_1$ is 3 carbons (as in VPA), sedative activity generally decreases as the length of the $R_2$ carbon chain increases. When $R_1$ is increased to 7 carbons, little or no sedative activity is seen.

EXAMPLE 3

Effect of Salts of M-VPA

Certain of the compounds of Example 2 were also tested as sodium salts. Specifically, VPA [M(3,3)], M(3,7) and M(3,10) were tested and are herein referred to as Na-VPA, Na-M(3,7) and Na-M(3,10) and for clarity. The free acid of each compound was stirred in the presence of sodium. The resulting salt had a high pH value of around 9–10. The salts were then dissolved in PBS (phosphate buffered saline, pH 7.4) to obtain a stock of 0.35M with a pH of about 8–8.5. Subsequent dilutions were usually done in saline. The doses administered were at 1.625 mmol/kg i.p. The animals were injected with the test compound 60 minutes before administration of 0.85 mg/kg s.c. PTZ and tested as in Example 2.

TABLE 2

Effect of Salts of M-VPA

| Compound | Dose (mg/kg) | Protection (number protected/total number) |
|---|---|---|
| Na-M(3,10) | 250 | 3/3 |
| Na-M(3,10) | 125 | 3/3 |
| Na-M(3,10) | 62.5 | 1/3 |
| Na-M(3,10) | 31.25 | 0/3 |
| Na-M(3,7) | 250 | 3/3 |
| Na-M(3,7) | 125 | 2/3 |
| Na-M(3,7) | 62.5 | 1/3 |
| Na-M(3,7) | 31.25 | 0/3 |

The key for Table 2 is as follows. Each drug was given at a concentration which was the molar equivalent to 500 mg/kg VPA, and therefore varied according to the molecular weight of the particular drug. Each drug was then rated for resultant anti-convulsive behavior in terms of the number of animals protected (the first term of the ratio) versus the total number of animals tested (the second term of the ratio).

Without desiring to be limited by any particular mechanism, these results probably occurred because salts of VPA and related molecules are absorbed into the system more quickly than the free acid, so that turnover is also faster. Lower doses of the pure salt form must also be given, since the same dosage level as for the free acid has extremely strong sedating effects. The free acid is absorbed more slowly, for a slow-release effect. Indeed, patients suffering from epilepsy are generally given a mixture of the free acid and the salt forms of VPA, in order to achieve maximum therapeutic efficacy over a longer period of time.

Figure 2:
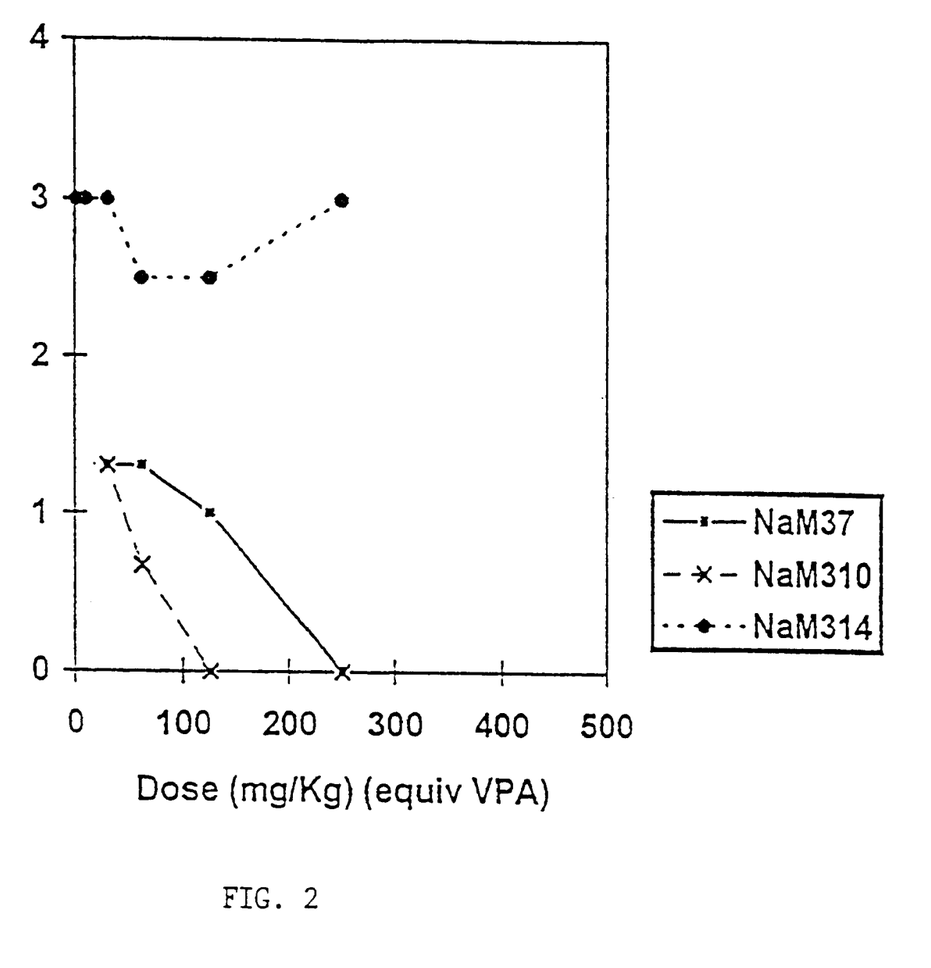
FIG. 2 is a graph showing dose-response to sodium salts of compounds of the present invention.

FIG. 2 shows a similar dose-response curve for the salts of M-VPA as in FIG. 1. Each point represents an average of three mice, except for the first concentration of Na-M(3,7), which represents five mice. Both Na-M(3,7) and Na-M(3, 10) exhibited anti-convulsive activity. The anti-convulsive activity of Na-M(3,7) was similar to that of M(3,7). However, the anti-convulsive activity of Na-M(3,10) was stronger than M(3,10).

From these results, a number of conclusions can be drawn. First, within the time scale of the experiment, the anti-convulsive activity of VPA is abolished by making the sodium salt, although the sedative activity is similar. Second, Na-M(3,7) is less sedating but has the same anti-convulsant activity of M(3,7). Finally, Na-M(3,10) is both more sedating and more anti-convulsive compared to M(3, 10). Thus, the sodium salts of M-VPA show similar, but not identical, activity to the M-VPA members of Example 2. Furthermore, the differences between the two groups of compounds varied according to the particular M-VPA member, rather than being characteristic of sodium salts of the group as a whole.

EXAMPLE 4

Synthesis of DP-M-VPA and Amide Analogs

As noted above, there are two strategies for reducing or eliminating unwanted side effects of a drug, such as valproic acid. The first strategy, described in Examples 1–3, involves manipulation of the pharmacophore. Such a strategy is widely used but is not always effective. Furthermore, this strategy is inefficient because of the untargeted, "hit or miss", approach. The second strategy is the use of an inactive or relatively less pharmaceutically active prodrug. This prodrug becomes activated in response to abnormally high levels of enzyme activity in the diseased tissue to be treated, thereby limiting the effects of the active molecule to those cells displaying such high activity.

The most useful strategy, and one which will be described in Examples 4 and 5, is a combination of both manipulating the pharmacophore and producing prodrugs of this altered pharmacophore. A group of prodrugs of M-VPA was synthesized according to the following method. These prodrugs, herein collectively referred to as "DP-M-VPA", have the following formula (IV):

(IV)

wherein:

$R_1$ is a saturated or unsaturated chain of 1–5 carbons in length; and $R_2$ is a saturated or unsaturated chain of 3–10 carbons in length, with the proviso that when is $R_1$ is 3 carbons in length, $R_2$ is a chain of 4–10 carbons in length; and L is a lipid moiety selected from the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lyso plasmalogens, lysophospholipids, lysophophatidic acid amides, glycerophosphoric acids, sphingolipids, lysophosphatidylethanolamine, and N-mono and N,N-di-($C_{1-4}$)alkyl derivatives of the amines thereof;

and pharmaceutically acceptable salts thereof.

Members of the DP-M-VPA are named as for the M-VPA group above. DP-VPA refers to the DP analog of VPA. DP-M(3,7) is the DP analog of M(3,7), and so forth. The synthetic procedure is as follows.

Synthesis of 1-O-Stearoyl-2-Propylheptylacetoyl-sn-Glycero-3-Phosphotidylcholine [DP-M(3,7)].

The synthesis of 1-O-stearoyl-2-O-propylheptylacetoyl-sn-glycero-3-phosphatidylcholine is a two-stage process. The first stage is a preparation of 2-propylnanoic anhydride. The final product is prepared by the second stage.

Stage 1. Synthesis of 2-Propylnonanoic Anhydride.

In a round-bottom single-neck flask (250 ml), equipped with a reverse condenser (water cooling) and magnetic stirrer, 2-propylnonoic acid (10 g, 0.5M), acetic anhydride (analytical, 400 ml, 1.06M) and pyridine (analytical, 44 ml, 0.5M) are introduced. This reaction mixture is stirred by magnetic stirrer for 4 hours at 700C. After that acetic anhydride is evaporated at a pressure of 20 mm Hg. Residue is distilled at 1 mm Hg and fraction which is boiling at 150–152° C. is collected. This is 2-propylnonanoic anhydride. 3 Yield is 85% (81.1 g).

Analyses: TLC is realized on plates of Silica gel 60 F254 (Merck). Eluent is chloroform (analytical). One spot is visible in UV spectra. Rf=0.89. Elementary analysis: $C_{24}H_{46}O_3$. Calculated: C 75.39%, H 12.04%. Found: C 75.25%, H 11.95%.

Stage II. Synthesis of 1-O-Stearoyl-2-O-2-Propylheptylacetoyl-sn-Glycero-3-Phosphotidylcholine.

Lyso-lecithin (1-stearoyl-sn-glycero-phosphotidylcholine; 2 g, 3.82 mM), sodium salt of valproic acid (0.7 g, 4.2 mM) and 2-propyl-nonanoic anhydride (20 ml) are introduced under argon in a round-bottom single-neck flask (500 ml), equipped with a reverse condenser (water cooling) and magnetic stirrer. The reaction mixture is heated in oil bath (80–100° C.) until disappearance of lyso-lecithin (TLC monitoring) in the solution (about 3 hours of heating). The unreacted valproic anhydride is then distilled from the reaction flask by heating (110–120° C.) under vacuum (about 0.1 mm Hg). The residue is dissolved in chloroform and the precipitate of sodium salt of valproic acid is separated from the solution by centrifugation. The obtained solution is concentrated by heating in an evaporator. After cooling, the chloroform solution of the reaction product is filtered on a chromatography column composed of Silica gel 60 (70–230 mesh). For purification of 1 gr. of raw reaction product 30 gr. of Silica gel are used. A mixture of chloroform, methanol and water (65:35:5 v/v) is used as an eluent. 2-propylheptyl acetic acid and its unreacted anhydride appear with the front of the eluent. The product is a white wax. After chromatography, purification of the product is washed by n-pentane (three washes, each using a portion of 20 ml). The obtained product is dried in vacuum at 40° C. Yield is 60% (1.5 g)

Analyses: TLC. Silica gel 60 F254 on aluminum sheet. Eluent is chloroform (stabilized by amylene) One spot is visible in UV spectra. Rf=0.3.

Elementary. $C_{38}H_{76}O_8NP$. Calculated: C 64.62%, H 10.77%, N 2.00%, P 4.39%. Found: C: 64.00%, H 10.9%, N 2.21%, P 4.4%.

1H NMR. (CDCL3), 6 (ppm): 0.86–0.92 (m, 9H), 1.26 (broad s, 42H), 1.42–1.44 (m, 2H), 1.53–1.61 (m, 4H), 2.24–2.34 (m, 3H), 3.38 (s, 9H), 3.81–4.45 (broad m, 8H) and 5.20-5.28 (m, 1H). 31P NMR (CDCL3), δ (ppm): −3.0 (respectively $H_3PO_4$ in $D_2O$) (s)

In addition, the amide analogs of the branched chain fatty acids were also synthesized. These analogs have the following formula (V):

(V)

wherein:
$R_1$ is a saturated or unsaturated chain of 1–5 carbons in length; and
$R_2$ is a saturated or unsaturated chain of 3–10 carbons in length, with the proviso that when is $R_1$ is 3 carbons in length, $R_2$ is a chain of 4–10 carbons in length; and R' and R" are each independently selected from the group consisting of hydrogen and a lower alkyl group comprising 1–5 carbon atoms;
and pharmaceutically acceptable salts thereof. The synthetic procedure is as follows.

The synthesis of these compounds is a two-step procedure. The chloride derivative of the branched chain fatty acid is prepared at the first stage, followed by the amide itself at the second stage. The synthesis of the amide of 2-propyloctadecanoic acid is given as an example of this procedure. The other amides are prepared according to an analagous procedure.

Overall, the synthesis can be described according to the following synthetic pathway:

2-Propyloctadecanoic acid (200 mg, 0.61 mmol) was introduced into a single neck round-bottom flask, equipped with a magnetic stirrer and a reverse condenser. Three milliliters of $SO_2Cl_2$ was also placed in the flask. The reaction mixture was brought to reflux and left for one hour. The reaction mixture was then evaporated. The dry benzene (5 ml) was added to the residue and then evaporated. This procedure was repeated twice. The resultant residue was dissolved in 5 ml of dry tetrahydrofuran and then 0.2 ml of 0.5 M ammonia in dioxane was added to this solution. The suspension thus obtained was stirred with the magnetic stirrer for one hour and then evaporated. Petroleum ether was added to the residue and the mixture was stirred. The obtained solid was filtered, and then washed by water and petroleum ether twice. The precipitate was dried under vacuum (10 mm Hg) for three hours at room temperature. The product was a white powder. The yield was 80%.

2-Propyl-nonamide

The product was a white powder with a yield of 75%.

Analyses: TLC. Silica gel 60 on aluminum sheet. Eluent was a mixture of petroleum ether with diethyl ether (3:7, v/v). Indicator was a spray of 4-methoxybenzaldehyde (10 ml), abs. ethanol (200 ml), 98% sulfuric acid (10 ml), glacial acetic acid (2 ml). The chromatogram was sprayed with this indicator, dried and then charred at 100–150° C. One spot was observed. $R_f$=0.2.

Chemical analysis. Elementary: $C_{12}H_{25}NO$. Calculated: C 72.36%, H 12.56%, N 7.04%. Found: C: 72.50%, H 12.81%, N 7.22%.

1H NMR. ($CDCL_3$), 5 (ppm): 0.85–0.94 (m, 6H), 1.22–1.42 (m, 14H), 1.51–1.60 (m, 2H), 2.06–2.18 (m, 1H) and 5.32–5.44 (d, 2H).

2-Propylhexadecanamide

The product was a white powder with a yield of 80%.

Analyses: TLC. Silica gel 60 on aluminum sheet. Eluent was a mixture of petroleum ether with diethyl ether (3:7, v/v). Indicator was a spray of 4-methoxybenzaldehyde (10 ml), abs. ethanol (200 ml), 98% sulfuric acid (10 ml), glacial acetic acid (2 ml). The chromatogram was sprayed with this indicator, dried and then charred at 100–150° C. One spot was observed. $R_f$=0.2.

Chemical analysis. Elementary: $C_{21}H_{43}NO$. Calculated: C 77.53%, H 13.23%, N 4.30%. Found: C 77.56%, H 13.39%, N 4.39%.

$^1H$ NMR. ($CDCL_3$), 6 (ppm): 0.86–0.92 (m, 6H), 1.24–1.43 (m, 30H), 1.52–1.60 (m, 4H), 2.08–2.12 (m, 1H) and 5.28–5.36 (d, 2H).

2-Propyloctadecanamide

The product was a white powder with a yield of 80%.

Analyses: TLC. Silica gel 60 on aluminum sheet. Eluent was a mixture of petroleum ether with diethyl ether (3:7, v/v). Indicator was a spray of 4-methoxybenzaldehyde (10 ml), abs. ethanol (200 ml), 98% sulfuric acid (10 ml), glacial acetic acid (2 ml). The chromatogram was sprayed with this indicator, dried and then charred at 100–150° C. One spot was observed. $R_f$=0.2.

Chemical analysis. Elementary: $C_{23}H_{47}NO$. Calculated: C 78.19%, H 13.31%, N 3.97%. Found: C 78.09%, H 13.11%, N 3.77%.

$^1H$ NMR. ($CDCL_3$), δ (ppm): 0.84–0.93 (m, 6H), 1.24–1.41 (m, 34H), 1.52–1.60 (broad s, 4H), 2.06–2.15 (m, 1H) and 5.30–5.36 (d, 2H).

EXAMPLE 5

Effect of DP-M-VPA

DP-M(3,7) was tested for its ability to inhibit convulsive activity and for its sedative effect. Molar equivalent doses were used. Since DP-M(3,7) is a larger molecule than DP-VPA, different amounts of the two drugs must be injected by weight in order to achieve the same dosage by moles. The following observations were made. First, when the equivalent dose of DP-M(3,7) was injected as in Example 2 into each of three mice, 60 minutes prior to PTZ injection, no protection from seizures was observed and all the mice died. However, when the dose was substantially increased to three times this level and was then given 90 minutes before PTZ to each of three mice, no seizures and no death was observed. However, the mice failed the rotorod test, indicating sedation, which continued up to 24 hours after injection of DP-M(3,7). Finally, when the dose was give 24 hours before the injection of PTZ to each of three mice, one short generalized clonic seizure was observed per animal, with no animal death.

Table 3 shows the results of an experiment with different doses of DP-M(3,7).

|  |  | # Convulsions/# Animals | |
| --- | --- | --- | --- |
| Dose (mg/kg) | Time pre-PTZ (hr) | First Convulsion | Second Convulsion |
| 27 | 1 | 3/3 | 2/3 |
| 27 | 21 | 3/3 | 2/3 |
| 100 | 1.5 | 2/3 | 1/3 |
| 100 | 24 | 2/3 | 2/3 |

The following should be noted about Table 3. First, all mice given 27 mg/kg DP-M(3,7) one hour before PTZ exhibited generalized clonic seizures. Such seizures were also seen if 27 mg/kg was given 21 hours before PTZ, and in 2/3 mice given 100 mg/kg 1.5 hours before PTZ. However, one mouse given 100 mg/kg 1.5 hours before PTZ had a much milder forelimbic (localized) seizure. When these same mice were given a second injection of PTZ 24 hours later, almost all seizures were forelimbic. Mice given 100 mg/kg 24 hours before PTZ had mainly generalized clonic seizures for the first seizure and forelimbic for the second seizure.

DP-M(3,7) was also tested on EP (epileptic prone) and ER (epileptically resistant) mice. EP mice are genetically prone to epileptic seizures, while ER mice are genetically resistant. In this experiment, DP-M(3,7) was injected as in Example 2, 24 hours before PTZ. The results were as follows. The first seizures in both EP and ER mice were generalized clonic. Treated EP mice had shorter seizure duration compared to untreated EP mice (2.25±2, n=4; 10.8±3 sec, n=4 for untreated mice; p<0.004, two-tailed students t-test). The seizure duration in ER mice was not significantly different from controls (8.75±2.3 sec vs 7.8±2 sec). DP-M(3,7) blocked second seizures in both EP and ER mice.

From these results, the following conclusions can be drawn. DP-M(3,7) is able to meliorate epileptic seizure activity induced by PTZ, by decreasing the severity of the seizure or by reducing its duration. The effect is stronger in mice given the test drug 24 hours before PTZ injection, and in mice given higher doses. Thus, DP-M(3,7) is able to inhibit convulsive activity induced by PTZ injection.

EXAMPLE 6

Suitable Formulations for Administration of VPA Analogs

The VPA analogs of the present invention, including M-VPA and DP-M-VPA, can be administered to a subject in a number of ways, which are well known in the art. Hereinafter the term "VPA analogs" refers to the group of M-VPA compounds and the group of DP-M-VPA compounds. Hereinafter, the term "subject" refers to the human or lower animal to whom the VPA analogs is administered. For example, administration may be done topically (including ophtalmically, vaginally, rectally, intranasally), orally, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on the severity of the symptoms and on the responsiveness of the subject to the VPA analog. Persons of ordinary skill in the art can easily determine optimum dosages, dosing methodologies and repetition rates.

EXAMPLE 7

Method of Treatment of Epilepsy

As noted above, the compounds of the present invention, which are analogs of VPA, have been shown to be an effective inhibitor of epileptic seizures. The following example is an illustration only of a method of treating epilepsy with the VPA analogs, and is not intended to be limiting.

The method includes the step of administering the VPA analog, in a pharmaceutically acceptable carrier as described in Example 6 above, to a subject to be treated. The VPA analog is administered according to an effective dosing methodology, preferably until a predefined endpoint is reached, such as the absence of further progression of the pathogenesis of epilepsy in the subject, or the prevention of epileptic seizures or abnormal brain activity.

EXAMPLE 8

Method of Manufacture of a Medicament Containing a VPA Analog

The following is an example of a method of manufacturing a VPA analog. First, the VPA analog is synthesized in accordance with good pharmaceutical manufacturing practice. Examples of methods of synthesizing the VPA analogs were given previously herein. Next, the VPA analog is placed in a suitable pharmaceutical carrier, as described in Example 6 above, again in accordance with good pharmaceutical manufacturing practice.

It will be appreciated that the above descriptions are intended only to serve as examples, and that many other embodiments are possible within the spirit and the scope of the present invention.

What is claimed is:

1. A method for the treatment of a central nervous system disorder in a subject, comprising the step of administering a pharmaceutically effective amount of a compound having the formula (I):

(I)

wherein:

$R_1$ is a saturated or unsaturated chain of 1–5 carbons in length; and $R_2$ is a saturated or unsaturated chain of 3–10 carbons in length; and A is selected from the group consisting of COOL and CONR'—R", wherein L is a lipid moiety selected form the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lyso plasmalogens, lysophospholipids, lysophophatidic acid amides, glycerophosphoric acids, sphingolipids, lysophosphatidylethanolamine, and N-mono and N,N-di-($C_{1-4}$)alkyl derivatives of the amines thereof; and when A is CONR'—R", R' and R" are each independently selected from the group consisting of hydrogen and a lower alkyl group comprising 1–5 carbon atoms, with the proviso that when $R_1$ is 2 or 3 carbons in length, $R_2$ is 4–10 carbons in length; and pharmaceutically acceptable salts thereof.

2. The method of claim 1, wherein $R_1$ is $(CH_2)_nCH_3$, n being 0–4; $R_2$ is $(CH_2)_xCH_3$, x being 2–9.

3. The method of claim 2, wherein n is 2 and x is 6–9.

4. The method of claim 2, wherein n is 2 and x is 6 or 9.

5. The method of claim 4, wherein n is 2 and x is 6.

6. The method of claim 1, wherein the central nervous system disorder is selected from the group consisting of epilepsy, mimes, pain and bipolar disorders.

7. A method for the treatment of a central nervous system disorder in a subject, comprising the step of administering a pharmaceutically effective amount of a compound having the formula (II):

(II)

wherein:

$R_1$ is a saturated or unsaturated chain of 1–5 carbons in length; and $R_2$ is a saturated or unsaturated chain of 4–10 carbons in length, with the proviso that when $R_1$ is $C_3H_7$, $R_2$ is not $C_4H_9$ or $C_5H_{11}$; and when $R_1$ is $C_4H_9$, $R_2$ is not $C_4H_9$;

and B is selected from the group consisting of COOH and COO$^-$Y$^+$, wherein Y denotes any pharmaceutically acceptable counter-ion;

and pharmaceutically acceptable salts thereof.

8. The method of claim 7, wherein $R_1$ is $(CH_2)$; $CH_3$, n being 0–4; $R_2$ is $(CH_2)_xCH_3$, x being 3–9.

9. The method of claim 8, wherein n is 2 and x is 6–9.

10. The method of claim 9, wherein n is 2 and x is 6 or 9.

11. The method of claim 10, wherein n is 2 and x is 6.

12. The method of claim 7, wherein the central nervous system disorder is selected from the group consisting of epilepsy, migranes, chronic pain and bipolar disorders.

13. A composition for treating a central nervous system disorder, comprising a pharmaceutically effective amount of a compound in combination with a pharmaceutically acceptable carriers said compound being a member of a group having the formula (II):

(II)

wherein:

$R_1$ is a saturated or unsaturated chain of 1–5 carbons in length; and $R_2$ is a saturated or unsaturated chain of 4–10 carbons in length, with the proviso that when $R_1$ is is $C_3H_7$, $R_2$ is not $C_4H_9$ or $C_5H_{11}$; and when $R_1$ is $C_4H_9$, $R_2$ is not $C_4H_9$; and B is selected from the group consisting of COOH and COO$^-$Y$^+$, wherein Y denotes any pharmaceutically acceptable counter-ion;

and pharmaceutically acceptable salts thereof.

14. The compound of claim 13, wherein $R_1$ is $(CH_2)_nCH_3$, n being 0–4, $R_2$ is $(CH_2)_xCH_3$, x being 3–9.

15. The composition of claim 14, wherein n is 2 and x is 6–9.

16. The composition of claim 15, wherein n is 2 and x is 6 or 9.

17. The composition of claim 16, wherein n is 2 and x is 6.

18. A compound having a formula (I):

(I)

wherein:

$R_1$ is a saturated or unsaturated chain of 1–5 carbons in length; and $R_2$ is a saturated or unsaturated chain of 3–10 carbons in length; and A is selected from the group consisting of COOL and CONR'—R", wherein L is a lipid moiety selected fromm the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lyso plasmalogens, lysophospholipids, lysophophatidic acid amides, glycerophosphoric acids, sphingolipids, lysophosphatidylethanolamine, and N-mono and N,N-di-($C_{1-4}$)alkyl derivatives of the amines thereof; and when A is CONR'—R". R' and R" are each independently selected from the group consisting of hydrogen and a lower alkyl group comprising 1–5 carbon atoms, with the proviso that when $R_1$ is 2 or 3 carbons in length, $R_2$ is 4–10 carbons in length; and pharmaceutically acceptable salts thereof.

19. The compound of claim 18, wherein $R_1$ is $(CH_2)_nCH_3$, n being 0–4; $R_2$ is $(CH_2)_xCH_3$, x being 2–9.

20. The compound of claim 19, wherein n is 2 and x is 6–9.

21. The compound of claim 19, wherein n is 2 and x is 6 or 9.

22. The compound of claim 21, wherein n is 2 and x is 6.

23. The compound of claim 18, wherein A is COOL.

24. A composition for treating a central nervous system disorder, comprising a pharmaceutically effective amount of a compound in combination with a pharmaceutically acceptable carrier, said compound being a member of a group having a formula (I):

wherein:

$R_1$ is a saturated or unsaturated chain of 1–5 carbons in length; and $R_2$ is a saturated or unsaturated chain of 3–10 carbons in length; and A is selected from the group consisting of COOL and CONR'—R", wherein L is a lipid moiety selected form the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lyso plasmalogens, lysophospholipids, lysophophatidic acid amides, glycerophosphoric acids, sphingolipids, lysophosphatidylethanolamine, and N-mono and N,N-di-($C_{1-4}$)alkyl derivatives of the amines thereof; and when A is CONR'—R", R' and R" are each independently selected from the group consisting of hydrogen and a lower alkyl group comprising 1–5 carbon atoms, with the proviso that when $R_1$ is 2 or 3 carbons in length. Ris 4–10 carbons in length; and pharmaceutically acceptable salts thereof.

25. The composition of claim 24, wherein $R_1$ is $(CH_2)_nCH_3$, n being 0–4; $R_2$ is $(CH_2)_xCH_3$, x being 2–9.

26. The composition of claim 25, wherein n is 2 and x is 6–9.

27. The composition of claim 25, wherein is 2 and x is 6 or 9.

28. The composition of claim 27, wherein n is 2 and x is 6.

* * * * *